(12) United States Patent
Stuiver et al.

(10) Patent No.: US 6,465,636 B1
(45) Date of Patent: Oct. 15, 2002

(54) PATHOGEN-INDUCIBLE PROMOTER

(75) Inventors: Maarten Hendrik Stuiver, Oegstgeest; Jerôme Hubertina Henricus Victor Custers, Alphen a/d Rijn; Lambertus Henricus Simons, Amstelveen, all of (NL)

(73) Assignee: Zeneca Mogen B.V., Leiden (NL)

( * ) Notice: Subject to any disclaimer, the term of this patent is extended or adjusted under 35 U.S.C. 154(b) by 0 days.

(21) Appl. No.: 09/647,390

(22) PCT Filed: Mar. 25, 1999

(86) PCT No.: PCT/EP99/02178

§ 371 (c)(1),
(2), (4) Date: Sep. 29, 2000

(87) PCT Pub. No.: WO99/50428

PCT Pub. Date: Oct. 7, 1999

(30) Foreign Application Priority Data

Apr. 1, 1998 (EP) .............................. 98201024

(51) Int. Cl.⁷ ........................... C07H 21/04; A01H 5/00
(52) U.S. Cl. ..................... 536/24.1; 800/279; 800/301; 800/295; 800/278; 435/410; 435/320.1
(58) Field of Search ....................... 536/24.1; 800/279, 800/301, 295, 278; 435/410, 320.1

(56) References Cited

FOREIGN PATENT DOCUMENTS

| EP | 0 307 841 | 3/1989 |
|---|---|---|
| EP | 0 337 532 | 10/1989 |
| WO | WP 96/28561 | 9/1996 |
| WO | WO 96/34949 | 11/1996 |
| WO | WO 98/03536 | 1/1998 |
| WO | WO 98/13478 | 4/1998 |
| WO | WO-9964562 | * 12/1999 |

OTHER PUBLICATIONS

Piano et al. Genetics, 152:605–616 (Jun. 1999).*

Facchini, P.J., et al., Plant Physiology, vol. 112, pp. 1669–1677, 1996.

Hauschild, K., et al., Plant Moelcular Biology, vol. 36, pp. 473–478, Feb. 1998.

Dittrich, H., et al., Proceedings of the National Academy of Sciences of the USA, vol. 88, pp. 9969–9973, 1991.

* cited by examiner

*Primary Examiner*—Jeffrey Fredman
*Assistant Examiner*—Juliet Einsmann
(74) *Attorney, Agent, or Firm*—Hale and Dorr LLP

(57) ABSTRACT

This invention describes pathogen-inducible promoters which normally drive expression of plant hexose oxidases, especially those which can be isolated from *Helianthus annuus* and *Lactuca sativa*, more specifically those promoters which naturally are the regulatory regions driving expression of the hexose oxidase MS59 and WL64, respectively. Also claimed are chimeric constructs where these pathogen-inducible promoters drive expression of antipathogenic proteins or of proteins which can elicit a hypersensitive response.

13 Claims, 1 Drawing Sheet

PATHOGEN-INDUCIBLE PROMOTER

FIELD OF THE INVENTION

This invention is related to the field of pathogen-inducible promoters, and chimeric DNA sequences comprising said promoters, especially in the area of plant biotechnology.

BACKGROUND ART

Inducible promoters include any promoter capable of increasing the amount of gene product produced by a given gene, in response to exposure to an inducer. In the absence of an inducer the DNA sequence will not be transcribed. Typically, the factor that binds specifically to an inducible promoter to activate transcription is present in an inactive form which is then directly or indirectly converted to the active form by the inducer. The inducer may be a chemical agent such as a protein, metabolite (sugar, alcohol, etc.), a growth regulator, herbicide, or a phenolic compound or a physiological stress imposed directly by heat, salt, wounding, toxic elements etc., or indirectly through the action of a pathogen or disease agent such as a virus. A plant cell containing an inducible promoter may be exposed to an inducer by externally applying the inducer to the cell such as by spraying, watering, heating, or similar methods. Inducible promoters are known to those familiar with the art and several exist that are be used to drive expression of genes of interest. Examples of inducible promoters include the inducible 70 kD heat shock promoter of *Drosophila melanogaster* (Freeling, M. et al., Ann. Rev. Genet. 19, 297–323) and the alcohol dehydrogenase promoter which is induced by ethanol (Nagao, R. T. et al., in: Miflin, B. J. (ed.) Oxford Surveys of Plant Molecular and Cell Biology, Vol. 3., pp. 384–438, Oxford Univ. Press, 1986). Examples for promoters that are inducible by a simple chemical are the promoters described in WO 90/08826, WO 93/21334, WO 93/031294 and WO 96/37609.

An important subclass of inducible promoters are the promoters which are induced in plants upon pathogen infection. As examples of a pathogen-inducible promoter the PRP1 promoter (also named gst1 promoter) obtainable from potato (Martini N. et al. (1993), Mol. Gen. Genet. 263, 179–186), the Fis1 promoter (WO 96/34949), the Bet v 1 promoter (Swoboda, I., et al., Plant, Cell and Env. 18, 865–874, 1995), the Vst1 promoter (Fischer, R., Dissertation, Univ. of Hohenheim, 1994; Schubert, R., et al. Plant Mol. Biol. 34, 417–426, 1997), the sesquiterpene cyclase promoter (Yin, S., et al., Plant Physiol. 115, 437–451, 1997) and the gstA1 promoter (Mauch, F. and Dudler, R., Plant Physiol. 102, 1193–1201, 1993) may be mentioned. A drawback of some of these promoters is that they are also active constitutively or that they do not react to certain types of pathogens. Furthermore, it would be advantageous to have promoters that regulate expression very soon after pathogen infection, i.e. with as short as possible induction times.

Thus, there is still need for promoters that are pathogen-inducible which overcome the disadavantages of the prior art.

SUMMARY OF THE INVENTION

We now have found DNA fragments which are the upstream regulatory regions for plant genes coding for hexose oxidase, capable of promoting pathogen-inducible transcription of an associated DNA sequence when re-introduced into a plant. Preferably such a fragment is obtainable from *Helianthus annuus*. Said DNA fragment specifically is the upstream regulatory region of the gene coding for hexose oxidase, denoted as MS59, more specifically characterized in that it comprises the nucleotide sequence from 1 to 1889 depicted in SEQ ID NO: 15.

Also part of the invention is a DNA fragment obtainable from *Lactuca sativa*, capable of promoting pathogen-inducible transcription of an associated DNA sequence when re-introduced into a plant, specifically the DNA fragment that it is the upstream regulatory region of the gene coding for hexose oxidase, denoted as WL64 (SEQ ID NO: 18).

Also included in the invention is a portion or variant of a DNA fragment according to any described above, capable of promoting pathogen-inducible transcription of an associated DNA sequence when re-introduced into a plant.

Embodiments of the invention are chimeric DNA sequences comprising in the direction of transcription a DNA fragment according to any one of the DNA fragments described above and a DNA sequence to be expressed under the transcriptional control thereof and which is not naturally under transcriptional control of said DNA fragment. A preferred embodiment is such a chimeric DNA sequence wherein the DNA sequence to be expressed causes the production of an antipathogenic protein, which is preferably selected from the group consisting of chitinase, glucanase, osmotin, magainins, lectins, saccharide oxidase, oxalate oxidase, toxins from *Bacillus thuringiensis*, antifungal proteins isolated from Mirabilis jalapa, Amaranthus, Raphanus, Brassica, Sinapis, Arabidopsis, Dahlia, Cnicus, Lathyrus, Clitoria, Allium seeds, Aralia and Impatiens and albumin-type proteins, such as thionine, napin, barley trypsin inhibitor, cereal gliadin and wheat-alpha-amylase.

Another embodiment of the chimeric DNA sequences of the invention is a chimeric DNA sequence wherein the DNA sequence to be expressed causes the production of a protein that can induce a hypersensitive response, preferably selected from the group consisting of CF and Pto proteins from tomato, avr proteins from *Cladosporium fulvum* and elicitor proteins from Pseudomonas or Xanthomonas.

Further part of the invention are replicons comprising above mentioned chimeric DNA sequences preferably having at least one recognition site for a restriction endonuclease for insertion of a DNA sequence to be expressed under the control of said DNA fragment. Also included in the invention are microorganisms containing such a replicon, plant cells having incorporated into their genome a chimeric DNA sequence according to those described above, and plants essentially consisting of said cells. such a plant is preferably a dicotyledonous plant. Also part of said plants selected from seeds, flowers, tubers, roots, leaves, fruits, pollen and wood, form part of the invention.

Yet another embodiment of the invention is the use of a DNA fragment as described above for identifying homologues capable of promoting pathogen-induced transcription in a plant.

Further use of a chimeric DNA sequence according to the invention for transforming plants and use of a portion or variant of the DNA fragments according to the invention for making hybrid regulatory DNA sequences is part of the invention.

Another object of the invention is the use of a chimeric DNA sequence as described above for conferring pathogen resistance to a plant.

DETAILED DESCRIPTION OF THE INVENTION

Figure 1:
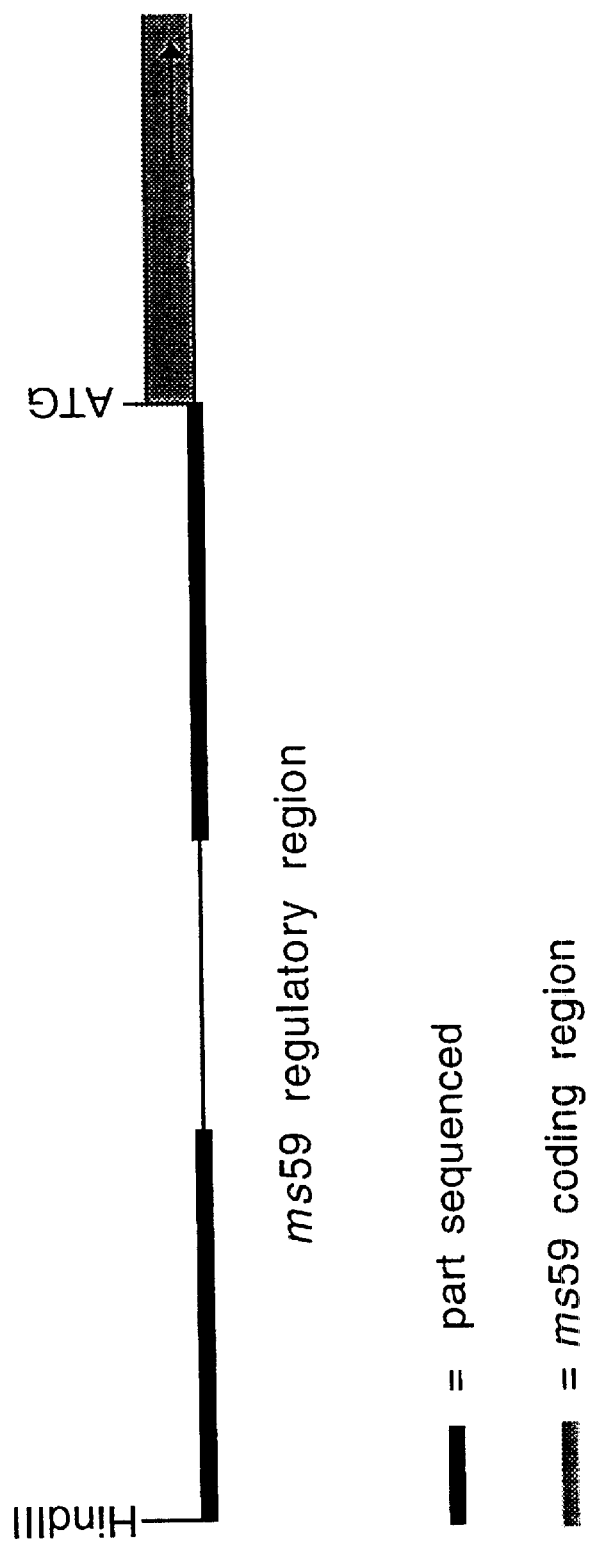
FIG. 1. Schematic drawing of (genomic) ms59 gene and promoter region.

The main aspect of the invention are regulatory sequences naturally occurring in plants and driving the expression of genes coding for hexose oxidase. Specifically the regions occurring in *Helianthus annuus* and/or *Lactuca sativa*, especially in the 5' (upstream) region of the MS59-gene (SEQ ID NO:15) or the WL64-gene (SEQ ID NO: 17), respectively. These genes encode a hexose oxidase which is found to be toxic to (fungal) pathogens, and they are disclosed in WO 98/13478, which is hereby inclosed for reference. It has been found that upon pathogen infection these genes are highly expressed, indicating pathogen inducibility. Pathogen inducible promoters are of great value in biotechnological resistance engineering.

Although the invention is exemplified especially with respect to the promoter driving the expression of the hexose oxidase in sunflower, denoted as 'ms59', it is believed that all promoters driving genes homologous to this ms59 will have properties that are more or less identical to the promoter of ms59, i.e. expression activity which is induced by pathogen infection, preferably by fungal infection. It is commonly known that promoters of homologous genes share similar properties, especially related to induction by pathogens. Examples of these are the promoters driving expression of the pathogenesis related protein osmotin, of which in potato (Zhu et al., Plant Physiol. 108, 929–937, 1995), in tobacco (Liu et al., Plant Mol. Biol. 29, 1015–1026, 1995) and in tomato (Ruiz-Medrano et al., Plant Mol. Biol. 20, 1199–1202, 1992) the inducibility by pathogens has been established; and promoters driving the expression of genes of the PR-10 group, of which the pSTH-2 promoter in potato (Matton, D. P. and Brisson, N, Mol. Plant-Microbe Interac. 2, 325–331, 1989), the AoPR-1 promoter in *Asparagus officinalis* (Warner, et al., The Plant J. 3, 191–201, 1993) and the Bet v 1 promoter in *Betula verrucosa* (Swoboda et al., Plant, Cell, Environm. 18, 865–874, 1995) have been shown to be pathogen inducible.

In this description the terms 'regulatory sequence' and 'promoter' are used interchangeably.

The present invention provides amongst others chimeric DNA sequences which comprise the regulatory sequences according to the invention. The expression chimeric DNA sequence shall mean to comprise any DNA sequence which comprises DNA sequences not naturally found in nature. For instance, chimeric DNA shall mean to comprise DNA comprising the regulatory region which is pathogen-inducible in a non-natural location of the plant genome, notwithstanding the fact that said plant genome normally contains a copy of the said regulatory region in its natural chromosomal location. Similarly, the said regulatory region may be incorporated in the plant genome wherein it is not naturally found, or in a replicon or vector where it is not naturally found, such as a bacterial plasmid or a viral vector. Chimeric DNA shall not be limited to DNA molecules which are replicable in a host, but shall also mean to comprise DNA capable of being ligated into a replicon, for instance by virtue of specific adaptor sequences, physically linked to the regulatory region according to the invention. The regulatory region may or may not be linked to its natural downstream open reading frame.

The open reading frame of the gene which expression is driven by the pathogen-inducible regulatory regions of the invention may be derived from a genomic library. In this latter it may contain one or more introns separating the exons making up the open reading frame that encodes a protein according to the invention. The open reading frame may also be encoded by one uninterrupted exon, or by a CDNA to the mRNA encoding a protein according to the invention. Chimeric DNA sequences according to the invention also comprise those in which one or more introns have been artificially removed or added. Each of these variants is embraced by the present invention.

In order to be capable of being expressed in a host cell a regulatory region according to the invention will usually be provided with a transcriptional initiation region which may be suitably derived from any gene capable of being expressed in the host cell of choice, as well as a translational initiation region for ribosome recognition and attachment. In eukaryotic cells, an expression cassette usually comprises in addition a transcriptional termination region located downstream of said open reading frame, allowing transcription to terminate and polyadenylation of the primary transcript to occur. In addition, the codon usage may be adapted to accepted codon usage of the host of choice. Further, often a signal sequence may be encoded, which is responsible for the targeting of the gene expression product to subcellular compartments. The principles governing the expression of a chimeric DNA construct in a chosen host cell are commonly understood by those of ordinary skill in the art and the construction of expressible chimeric DNA constructs is now routine for any sort of host cell, be it prokaryotic or eukaryotic.

In order for the chimeric DNA sequence to be maintained in a host cell it will usually be provided in the form of a replicon comprising said chimeric DNA sequence according to the invention linked to DNA which is recognised and replicated by the chosen host cell. Accordingly, the selection of the replicon is determined largely by the host cell of choice. Such principles as govern the selection of suitable replicons for a particular chosen host are well within the realm of the ordinary skilled person in the art.

A special type of replicon is one capable of transferring itself, or a part thereof, to another host cell, such as a plant cell, thereby co-transferring the open reading frame according to the invention to said plant cell. Replicons with such capability are herein referred to as vectors. An example of such vector is a Ti-plasmid vector which, when present in a suitable host, such as *Agrobacterium tumefaciens*, is capable of transferring part of itself, the so-called T-region, to a plant cell. Different types of Ti-plasmid vectors (vide: EP 0 116 718 B1) are now routinely being used to transfer chimeric DNA sequences into plant cells, or protoplasts, from which new plants may be generated which stably incorporate said chimeric DNA in their genomes. A particularly preferred form of Ti-plasmid vectors are the so-called binary vectors as claimed in (EP 0 120 516 B1 and U.S. Pat. No. 4,940, 838). Other suitable vectors, which may be used to introduce DNA according to the invention into a plant host, may be selected from the viral vectors, e.g. non-integrative plant viral vectors, such as derivable from the double stranded plant viruses (e.g. CaMV) and single stranded viruses, gemini viruses and the like. The use of such vectors may be advantageous, particularly when it is difficult to stably transform the plant host. Such may be the case with woody species, especially trees and vines.

The expression "host cells incorporating a chimeric DNA sequence according to the invention in their genome" shall mean to comprise cells, as well as multicellular organisms comprising such cells, or essentially consisting of such cells, which stably incorporate said chimeric DNA into their genome thereby maintaining the chimeric DNA, and preferably transmitting a copy of such chimeric DNA to progeny cells, be it through mitosis or meiosis. According to a preferred embodiment of the invention plants are provided, which essentially consist of cells which incorporate one or more copies of said chimeric DNA into their genome, and which are capable of transmitting a copy or copies to their progeny, preferably in a Mendelian fashion. By virtue of the transcription and translation of the chimeric DNA according to the invention in some or all of the plant's cells, those cells that comprise said regulatory region will respond to pathogen attack and thus produce the protein encoded by the open reading frame which is under control of the regulatory region. In specific embodiments of the invention this protein will be an antipathogenic protein which is capable of conferring resistance to pathogen infections.

As is well known to those of skill in the art, regulatory regions of plant genes consist of disctinct subregions with interesting properties in terms of gene expression. Examples of subregions as meant here, are enhancers but also silencers of transcription. These elements may work in a general (constitutive) way, or in a tissue-specific manner. Deletions may be made in the regulatory DNA sequences according to the invention, and the subfragments may be tested for expression patterns of the associated DNA. Various subfragments so obtained, or even combinations thereof, may be useful in methods of engineering pathogen resistance, or other applications involving the expression of heterologous DNA in plants. The use of DNA sequences according to the invention to identify functional subregions, and the subsequent use thereof to promote or suppress gene expression in plants is also encompassed by the present invention.

As regards the necessity of a transcriptional terminator region, it is generally believed that such a region enhances the reliability as well as the efficiency of transcription in plant cells. Use thereof is therefore strongly preferred in the context of the present invention.

Examples of proteins that may be used in combination with the ICS regulatory region according to the invention include, but are not limited to, β-1,3-glucanases and chitinases which are obtainable from barley (Swegle M. et al., Plant Mol. Biol. 12, 403–412, 1989; Balance G. M. et al. , Can. J. Plant Sci. 56, 459–466, 1976; Hoj P. B. et al., FEBS Lett. 230, 67–71, 1988; Hoj P. B. et al. , Plant Mol. Biol. 13, 31–42, 1989), bean (Boller T. et al. , Planta 157, 22–31, 1983; Broglie K. E. et al., Proc. Natl. Acad. Sci. USA 83, 6620–6824, 1986; Vogeli U. et al., Planta 174, 364–372, 1988); Mauch F. & Staehelin L. A., Plant Cell 1, 447–457, 1989); cucumber (Metraux J. P. & Boller T., Physiol. Mol. Plant Pathol. 28, 161–169, 1986); leek (Spanu P. et al., Planta 177, 447–455, 1989); maize (Nasser W. et al., Plant Mol. Biol. 11, 529–538, 1988), oat (Fink W. et al., Plant Physiol. 88, 270–275, 1988), pea (Mauch F. et al., Plant Physiol. 76, 607–611, 1984; Mauch F. et al., Plant Physiol. 87, 325–333, 1988), poplar (Parsons, T. J. et al., Proc. Natl. Acad. Sci. USA 86, 7895–7899, 1989), potato (Gaynor J. J., Nucl. Acids Res. 16, 5210, 1988; Kombrink E. et al., Proc. Natl. Acad. Sci. USA 85, 782–786, 1988; Laflamme D. and Roxby R., Plant Mol. Biol. 13, 249–250, 1989), tobacco (e.g. Legrand M. et al., Proc. Natl. Acad. Sci. USA 84, 6750–6754, 1987; Shinshi H. et al. Proc. Natl. Acad. Sci. USA 84, 89–93, 1987), tomato (Joosten M. H. A. & De Wit P. J. G. M., Plant Physiol. 89, 945–951, 1989), wheat (Molano J. et al., J. Biol. Chem. 254, 4901–4907, 1979), magainins, lectins, toxins isolated from *Bacillus thuringiensis*, antifungal proteins isolated from *Mirabilis jalapa* (EP 0 576 483) and Amaranthus (EP 0 593 501 and U.S. Pat. No. 5,514,779), albumin-type proteins (such as thionine, napin, barley trypsin inhibitor, cereal gliadin and wheat-alpha-amylase, EP 0 602 098), proteins isolated from Raphanus, Brassica, Sinapis, Arabidopsis, Dahlia, Cnicus, Lathyrus and Clitoria (EP 0 603 216), proteins isolated from Capsicum, Briza, Delphinium, Catapodium, Baptisia and Microsensis (PCT/GB93/02179), oxalate oxidase (EP 0 636 181 and EP 0 673 416), saccharide oxidase (PCT/EP 97/04923), antimicrobial proteins isolated from Allium seeds (PCT/GB94/01636), proteins from Aralia and Impatiens (PCT/GB95/00509), proteins from Heuchera and Aesculus (PCT/GB94/02766), mutant peptides to the above mentioned proteins (PCT/GB96/03065 and PCT/GB96/03068) and the like.

Another use of the inducible promoter is to drive proteins which play a role in the gene-for-gene resistance interaction (e.g. as described in WO 91/15585). Such proteins are, for example, plant proteins such as disclosed in Karrer, E. E. et al. (Plant Mol. Biol. 36, 661–690, 1998), activated ndr1, activated eds1 and activated Xa21, Cf-proteins, BS3 protein and Pto proteins from tomato, Rpm1 and Rps2 proteins from *Arabidopsis thaliana*, the N-gene from tobacco, the avr-elicitor proteins from *Cladosporiur fulvum*, avrBs3 from Xanthomonas, harpins from Erwinia and the avrPto protein from Pseudomonas.

The actual applicability of the invention is not limited to certain plant species. Any plant species that is subject to some form of pathogen attack, may be transformed with chimeric DNA sequences according to the invention, allowing the regulatory region to be induced by pathogen infection thereby triggering production of antipathogenic proteins to be produced in some or all of the plant's cells.

Although some of the embodiments of the invention may not be practicable at present, e.g. because some plant species are as yet recalcitrant to genetic transformation, the practicing of the invention in such plant species is merely a matter of time and not a matter of principle, because the amenability to genetic transformation as such is of no relevance to the underlying embodiment of the invention.

Transformation of plant species is now routine for an impressive number of plant species, including both the Dicotyledoneae as well as the Monocotyledoneae. In principle any transformation method may be used to introduce chimeric DNA according to the invention into a suitable ancestor cell, as long as the cells are capable of being regenerated into whole plants. Methods may suitably be selected from the calcium/polyethylene glycol method for protoplasts (Krens, F. A. et al., Nature 296, 72–74, 1982; Negrutiu I. et al, , Plant Mol. Biol. 8, 363–373, 1987), electroporation of protoplasts (Shillito R. D. et al., Bio/Technol. 3, 1099–1102, 1985), microinjection into plant material (Crossway A. et al., Mol. Gen. Genet. 202, 179–185, 1986), DNA (or RNA-coated) particle bombardment of various plant material (Klein T. M. et al., Nature 327, 70, 1987), infection with (non-integrative) viruses and the like. A preferred method according to the invention comprises Agrobacterium-mediated DNA transfer. Especially preferred is the use of the so-called binary vector technology as disclosed in EP A 120 516 and U.S. Pat. No. 4,940,838.

Tomato transformation is preferably done essentially as described by Van Roekel et al. (Plant Cell Rep. 12, 644–647, 1993). Potato transformation is preferably done essentially as described by Hoekema et al. (Hoekema, A. et al., Bio/Technology 7, 273–278, 1989). Generally, after transformation plant cells or cell groupings are selected for the presence of one or more markers which are encoded by plant expressible genes co-transferred with the nucleic acid sequence encoding the protein according to the invention, whereafter the transformed material is regenerated into a whole plant.

Although considered somewhat more recalcitrant towards genetic transformation, monocotyledonous plants are amenable to transformation and fertile transgenic plants can be regenerated from transformed cells or embryos, or other plant material. Presently, preferred methods for transformation of monocots are microprojectile bombardment of embryos, explants or suspension cells, and direct DNA uptake or electroporation (Shimamoto, et al, Nature 338, 274–276, 1989). Transgenic maize plants have been obtained by introducing the *Streptomyces hygroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, Plant Cell, 2, 603–618, 1990). The introduction of genetic material into aleurone protoplasts of other monocot crops such as wheat and barley has been reported (Lee, Plant Mol. Biol. 13, 21–30, 1989). Wheat plants have been regenerated from embryogenic suspension culture by selecting only the aged compact and nodular embryogenic callus tissues for the establishment of the embryogenic suspension cultures (Vasil, Bio/Technol. 8, 429–434, 1990). The combination with transformation systems for these crops enables the application of the present invention to monocots.

Monocotyledonous plants, including commercially important crops such as rice and corn are also amenable to DNA transfer by Agrobacterium strains (vide WO 94/00977; EP 0 159 418 B1; Gould J, et al., Plant. Physiol. 95, 426–434, 1991).

Following DNA transfer and regeneration, putatively transformed plants may be evaluated, for instance using Southern analysis, for the presence of the chimeric DNA according to the invention, copy number and/or genomic organization. In addition, or alternatively, expression levels of the newly introduced DNA may be undertaken, using Northern and/or western analysis, techniques well known to persons having ordinary skill in the art. After the initial analysis, which is optional, transformed plants showing the desired copy number and expression level of the newly introduced chimeric DNA according to the invention may be tested for resistance levels against pathogens. Alternatively, the selected plants may be subjected to another round of transformation, for instance to introduce further genes, in order to enhance resistance levels, or broaden the resistance.

Other evaluations may include the testing of pathogen resistance under field conditions, checking fertility, yield, and other characteristics. Such testing is now routinely performed by persons having ordinary skill in the art.

Following such evaluations, the transformed plants may be grown directly, but usually they may be used as parental lines in the breeding of new varieties or in the creation of hybrids and the like.

To obtain transgenic plants capable of constitutively expressing more than one chimeric gene, a number of alternatives are available including the following:

A. The use of DNA, e.g a T-DNA on a binary plasmid, with a number of modified genes physically coupled to a selectable marker gene. The advantage of this method is that the chimeric genes are physically coupled and therefore migrate as a single Mendelian locus.

B. Cross-pollination of transgenic plants each already capable of expressing one or more chimeric genes, preferably coupled to a selectable marker gene, with pollen from a transgenic plant which contains one or more chimeric genes coupled to another selectable marker. Afterwards the seed, which is obtained by this crossing, maybe selected on the basis of the presence of the two selectable markers, or on the basis of the presence of the chimeric genes themselves. The plants obtained from the selected seeds can afterwards be used for further crossing. In principle the chimeric genes are not on a single locus and the genes may therefore segregate as independent loci.

C. The use of a number of a plurality chimeric DNA molecules, e.g. plasmids, each having one or more chimeric genes and a selectable marker. If the frequency of co-transformation is high, then selection on the basis of only one marker is sufficient. In other cases, the selection on the basis of more than one marker is preferred.

D. Consecutive transformation of transgenic plants already containing a first, second, (etc) chimeric gene with new chimeric DNA, optionally comprising a selectable marker gene. As in method B, the chimeric genes are in principle not on a single locus and the chimeric io genes may therefore segregate as independent loci.

E. Combinations of the above mentioned strategies

The actual strategy may depend on several considerations as maybe easily determined such as the purpose of the parental lines (direct growing, use in a breeding programme, use to produce hybrids) but is not critical with respect to the described invention.

In this context it should be emphasised that plants already containing chimeric DNA may form a suitable genetic background for introducing further chimeric DNAs according to the invention, for instance in order to enhance the production antipathogenic substances, thereby enhancing resistance levels. The cloning of other genes corresponding to proteins that can suitably be used in combination with the regulatory DNA fragments, and the obtention of transgenic plants, capable of relatively over-expressing same, as well as the assessment of their effect on pathogen resistance in planta, is now within the scope of the ordinary skilled person in the art.

Plants with improved resistance against pathogens may be grown in the field, in the greenhouse, or at home or elsewhere. Plants or edible parts thereof may be used for animal feed or human consumption, or may be processed for food, feed or other purposes in any form of agriculture or industry. Agriculture shall mean to include horticulture, arboriculture, flower culture, and the like. Industries which may benefit from plant material according to the invention include but are not limited to the pharmaceutical industry, the paper and pulp manufacturing industry, sugar manufacturing industry, feed and food industry, enzyme manufacturers and the like. The advantages of the plants, or parts thereof, according to the invention are the decreased need for biocide treatment, thus lowering costs of material, labour, and environmental pollution, or prolonginc shelf-life of products (e.q. fruit, seed, and the like) of such plants. Plants for the purpose of this invention shall mean multicellular organisms capable of photosynthesis, and subject to some form of pathogen attack. They shall at least include angiosperms as well as gymnosperms, monocotyledonous as well as dicotyledonous plants.

EXAMPLE 1

Induction of ms59 Messengers in Sunflower Plants

Leaves of 7 to 8 weeks old Sunflower plants (*Helianthus annuus* cv Zebulon) were induced by spraying 5 times with 5 mM salicylic acid (SA), spraying once with 1 mM salicylic acid, once with 0.1 mm jasmonic acid (JA), once with 1 mM ACC (1-aminocyclopropane-1-carboxylic acid, a precursor of the plant hormone ethylene) or wounding. Leaf samples were harvested from induced leaves after 24 hours (1 mM SA, 0.1 mM JA, 1 mM ACC and wounding) and after 5 days (5 mM SA). Control samples were taken at 24 hours after induction in non-induced plants.

EXAMPLE 2

RNA Extraction from Sunfower Leaf Tissue and cDNA Synthesis

Total RNA was extracted from 10 g leaf material using a hot phenol method and purified using the Qiagen RNA buffer set and tip-100 columns (Qiagen GmbH, Germany). Contaminating DNA was degraded using a Dnase I (Gibco BRL) treatment.

cDNA was prepared using 1 µg total RNA, 1 µl oligo(dT)$_{12-18}$ primers (500 µg/ml, Gibco BRL) and 200 units of Superscript II RT RNAse H reverse transcriptase (Gibco BRL) as described by the manufacturer.

EXAMPLE 3

Construction of ms59 PCR MIMIC and Analysis of Samples by Competitive RT-PCR Transcript levels of ms59 were determined using the competitive RT-PCR technology. In this technique competition between the cDNA target and an artificial PCR MIMIC makes quantitation of transcript levels possible (Paul D. Siedert and James W. Larrick (1992), Nature 359, 557–558).

For construction of a PCR MIMIC the following primers were developed; FR-pUC-208 (SEQ ID NO: 1) 5' GTT CCG GAG GTT GTG ACC GTG GGA TGT GCT GCA AGG CG3', FR-pUC-209 (SEQ ID NO: 2) 5' CTG GGG AAG CCC GTG TAG TAA AGC CCC CGC GCG TTG GCC GAT TC3', FR-MS59-47 (SEQ ID NO: 3) 5' CTG GGG AAG CCC GTG TAG TAA AGC3' and FR-MS59-77 (SEQ ID NO: 4) 5' GTT CCG GAG GTT GTG ACC GTG3', Primers FR-pUC-208 and FR-pUC-209 were used to amplify a fragment of 387 bp from the plasmid pUC18 (Yanisch-Perron, C., Vieira, J. and Messing, J. (1985) Gene 33, 103–119) by PCR (10 cycles of 1' 95° C., 1' 55° C., 2' 72° C.) From this PCR product 1 µl was amplified using primers FR-MS59-47 and FR-MS59-77 by PCR to produce a large amount of PCR MIMIC (30 cycles of 1' 95° C., 1' 55° C., 2' 72° C.).

Primers FR-MS59-47 and FR-MS59-77 will amplify a band of 312 bp from the ms59 CDNA so it can be distinguished easily from the 387 bp MIMIC when separated on a 2% agarose gel. PCR MIMIC dilutions were made in a range of 100 ng/pl to 0.01 ag/µl in H$_2$O containing 0.2 µg/µl glycogen as a carrier.

TABLE 1

Induction levels of the ms59 messenger in sunflower leaves after different stress treatments relative to the control.

| Induction method | fold induction |
| --- | --- |
| Control | 1[a] |
| 5 mM salicylic acid | 1000 |
| 1 mM salicylic acid | 1[a] |
| 1 mM ACC | 10 |
| 0.1 mM jasmonic acid | 10 |
| wounding | 10 | note: [a]: could not be detected, arbitrary set to 1.

The cDNA samples were analysed in a competitive RT-PCR. Therefore 2 µl of the samples was combined in a 0.5 ml tube with 1 µl diluted PCR MIMIC (amounts; 0.1 pg, 10 fg, 1.0 fg, 0.1 fg, 10 ag and 1.0 ag). Amplification of cDNA and MIMIC was performed using 10 µM of the primers FR-MS59-47 and FR-MS59-77, 0.5 µl 20 mM dNTP's, 1×PCR buffer, MgCl and 2.5 units recombinant Taq DNA polymerase (Gibco BRL) and was allowed to proceed for 35 cycles, 1' 95° C., 1' 55° C., 2' 72° C. PCR products were separated on a 2% agarose gel and visualized by staining with ethidium bromide and a UV illuminator.

EXAMPLE 4

Infection Assays in Sunflower Plants with Different Fungi

Fungal infections were performed on plants of 7 to 8 weeks old. Leaves were inoculated by laying small droplets (15–20 µl) of a Botrytis cinerea spore suspension, *Diaporthe helianthi* (PH9905) hyphal fragment supension or a *Sclerotinia sclerotiorum* hyphal fragment supsension on small cuttings made in the leaf to enable the fungi to penetrate the plant. Fungal infections were allowed to proceed at 18° C. and a high relative humidity (±90%). Leaf disks (diameter= 13 mm) harbouring the site of infection were harvested at approximately 4 days after inoculation. Around the hole of the first small leaf disk, a further ring of 25 mm was harvested. Leaf disks were also harvested in non-infected leaves around leaf cuttings as a control.

EXAMPLE 5

PolyA$^+$-RNA Extraction from Sunfower Leaf Tissue and CDNA Synthesis

Poly-A$^+$ RNA was harvested from 100 mg of leaf tissue using the Quickprep Micro mRNA purification Kit (Amersham Pharmacia Biotech, Uppsala, Sweden). The relative amount of MRNA was determined using visualisation of nucleic acids by spotting 10 µl of the samples with 4 µl 1 µg/ml ethidium bromide on a UV illuminator. Equal amounts of Poly-A$^+$ RNA (±100 ng) were used to synthesize cDNA using 200 units of Superscript II RT RNAse H reverse transcriptase (Gibco BRL) and 1 µl oligo(dT)$_{12-18}$ primers (500 µg/ml, Gibco BRL) as described by the manufacturer.

EXAMPLE 6

Analysis of Samples by Competitive RT-PCR

The different cDNA samples were analysed as described in example 3.

TABLE 2

Induction levels of the ms59 messenger after infection of sunflower leaves with different fungi.

| Sample | fold induction leaf disk[b] | fold induction outer infection area[c] |
| --- | --- | --- |
| Control | 1[a] | 1[a] |
| Diaporthe helianthi | 1000 | 1000 |
| Botrytis cinerea | 1000 | 1[a] |
| Sclerotinia sclerotiorum | 1000 | 1[a] | note: [a]: arbitrary set to 1.
[b]: leaf disk of 13 mm around site of fungal infection.
[c]: leaf ring from 13 mm to 25 mm around site of fungal infection.

EXAMPLE 7

Construction of a Sunflower gapC PCR MIMIC and Analysis of Samples by Competitive RT-PCR As an internal control on the quality of the mRNA and preparation of 15 CDNA we included a competitive RT-PCR on the housekeeping gene GapC using the same samples as described in examples 4, 5 and 6. For the construction of a PCR MIMIC the following primers were developed; FR-pUC-224 (SEQ ID NO: 5) 5' CCA TGG GCT CAA ACT GGA-GCC GGC CGG GAG CAG ACA AGC CCG 3', FR-pUC-225 (SEQ ID NO: 6) 5' CGA GAC GTC AAC AGT CGG GAC CCA CTC ATT AGG CAC CCC AGG C3', FR-gapC-211 (SEQ ID NO: 7) 5' CCA TGG GCT CAA ACT GGA GCC G3' and FR-gapC-212 (SEQ ID NO: 8) 5' CGA GAC GTC AAC AGT CGG GAC C3'. Primers FR-pUC-224 and FR-pUC-225 were used to amplify a fragment of 527 bp from the plasmid pUC18 (Yanisch-Perron, C., Vieira, J. and Messing, J. (1985) Gene 33, 103–119) by PCR (10 cycles of 1' 95° C., 1' 55° C., 2' 72° C.). From this PCR product 1 µl was amplified using primers FR-gapC-211 and FR-gapC-212 by PCR to produce a large amount of PCR MIMIC (30 cycles of 1' 95° C., 1' 55° C., 2' 72° C.).

Primers FR-gapC-211 and FR-gapC-212 will amplify a band of 470 bp from the gapc cDNA so it can be distinguished easily from the 527 bp MIMIC when separated on a 2% agarose gel. PCR MIMIC dilutions were made in a range of 100 ng/pl to 0.01 ag/pl in $H_2O$ containing 0.2 µg/µl glycogen as a carrier.

The cDNA samples were analysed in a competitive RT-PCR. Therefore 2 µl of each sample was combined in a 0.5 ml tube with 1 µl diluted PCR MIMIC (amounts; 0.1 pg, 10 fg, 1.0 fg, 0.1 fg, 10 ag and 1.0 ag) Amplification of cDNA and MIMIC was performed using 10 µM of the primers FR-gapC-211 and FR-gapC-212, 0.5 µl 20 mM dNTP's, 1×PCR buffer, $MgCl_2$ and 2.5 units recombinant Taq DNA polymerase (Gibco BRL) and was allowed to proceed for 35 cycles, 1' 95° C., 1' 55° C., 2' 72° C. PCR products were separated on a 2% agarose gel and visualized by staining with ethidium bromide and a UV illuminator.

TABLE 3

Induction levels of the control GapC messenger after infection of sunflower leaves with different fungi.

| Sample | fold induction in 13 mm leaf disks |
|---|---|
| Control | 1[a] |
| Diaporthe helianthi | 10 |
| Botrytis cinerea | 10 |
| Sclerotinia sclerotiorum | 10 | note: [a]: arbitrary set to 1.

The results show that RNA quality and CDNA preparation is not affected by these fungal infections. Induction of GapC messengers by plant pathogens and environmental stress factors was described before in Laxalt et al., (1996) Plant Mol. Biol. 30: 961–972.

EXAMPLE 8

Isolation of the ms59 Promoter from the Sunflower Genome

For the isolation of the ms59 promoter genomic DNA was isolated from sunflower leaves using a CTAB extraction procedure. About 10 µg of genomic DNA was digested with the restriction enzymes BspH I, EcoR V, Nla IV, Hph I, Rsa I, Ssp I and Hind III for 16 hours at 37° C. These restriction sites are all located within the first part of the ms59 cDNA. The digestion mixtures were extracted with 1 volume phenol:chloroform:isoamylalcohol (25:24:1, v/v, Gibco BRL) and precipitated with 0.1 volume of 3 M NaAc (pH=5.2) and 2.5 volumes of 96% ethanol. The DNA pellet was washed with 70% ethanol and the pellet was then dissolved in 50 pl distilled water.

25 µl of each sample was separated on a 0.7% agarose gel for 16 hours at 40 volts. The DNA was transferred to a nylon membrane (Hybond-N+, Amersham Life Science) using southern blotting with 0.4 M NaOH. The blot was hybridized (16 hours, 65° C.) using a 320 bp fragment (from the ATG startcodon until the BspH I site) labeled with $^{32}$P-dCTP as a probe. Then the blot was washed with a stringency of 0.2×SSc at 65° C. The results of the southern blot are listed in table 4.

The remaining 25 µl of digestion mixture was ligated in such a way that circularization of the DNA fragments was stimulated. This was done by ligating the DNA in a (large) volume of 300 µl in 1×T4 ligation buffer and 5 weiss units of T4 DNA ligase (Gibco BRL) for 16 hours at 16° C. Again the mixture was extracted with phenol:chloroform:isoamylalcohol and precipitated with ethanol and the DNA pellet was dissolved in 50 µl $H_2O$.

Primers were designed within the first part of the CDNA (between the ATG startcodon and the first restriction site used (BspH I) and directed outwards. Primers FR-MS59-11 (SEQ ID NO: 9) 5' CAG GCA GCT GTG GTT TGT GGC3' and FR-MS59-49 (SEQ ID NO: 10) 5' CGG GAA GTT GCA GAA GAT TGG GTT G3' were used in a PCR reaction on 1 µl of the ligation mixture using the Advantage Klentaq polymerase mix (Clontech laboratories, Inc., Palo Alto, Calif.) 200 µM dNTP's and 10 µM of each primer. The polymerase mix was activated for 1' at 94° C. followed by 35 cycles of amplification for 30" at 94° C., 1' at 55° C. and 3' at 68° C. The PCR products were analysed on a 1% agarose gel and no specific band could be detected. Therefore nested PCR was performed as described above but now with nested primers FR-MS59-34 (SEQ ID NO: 11) 5' ACG TAG ATA TCG AAC AAG AAA CCG C3' and FR-MS59-50 (SEQ ID NO: 12) 5' GAG CAA GAG AAG AAG GAG AC3' using 1 µl of the PCR product from the first PCR round. After analysis of the PCR products on a 1% agarose gel very specific single bands were detected. Inverse PCR results are listed in table 4.

TABLE 4

Results inverse PCR and southern blot band sizes (nd = not determined)

| Inverse PCR restriction enzyme | Band sizes southern blot | Band sizes nested PCR |
|---|---|---|
| BspH I | >7 kb | nd |
| EcoR V | >7 kb | nd |
| Nla IV | 1.0 kb | 0.6 kb |
| Hph I | 1.2 kb | 0.8 kb |
| Rsa I | 0.5 kb | 0.2 kb |
| Ssp I | 1.3 kb | 0.9 kb |
| Hind III | 2.3 kb | 1.9 kb |

The 1.9 kb Hind III iPCR band was isolated from gel and the DNA sequence of the ends was determined using primers FR-MS59-34 and FR-MS59-50 on a automatic DNA sequencer (Applied Biosystems).

Based on the DNA sequence new primers were designed for the amplification of the ms59 promoter region from the sunflower genome. Primer FR-MS59-226 (SEQ ID NO: 13) 5' GCA AGC TTT ATA GTT TAC GAT CC3' is directed downstream, located in the upstream part of the ms59 promoter region overlapping the Hind III restriction site.

Primer FR-MS59-227 (SEQ ID NO: 14) 5' TTG CCA TGG TGC ATG GTT TAG CG3' can anneal at the most downstream part of the ms59 promoter/leader overlapping the ATG translational start introducing a Nco I restriction site spanning the ATG startcodon. The DNA sequence of the complete promoter fragment from the upstream Hind III to Nco I site (SEQ ID NO: 15, nucleotides 1–1889) was determined using automated DNA sequence analysis (Applied Biosystems).

Using Pfu DNA polymerase (Stratagene) and both primers the ms59 promoter region was amplified from sunflower genomic DNA. The 1.9 kb PCR product was digested with Hind III and Nco I and ligated in a multicopy cloning vector also digested with Hind III and Nco I. The promoter was fused to the GUSintron reporter gene (Jefferson et al., (1987) EMBO J 6: 3901–3907) followed by the 3' untranslated region of the potato proteinase inhibitor II gene (Thornburg et al., 1987, Proc. Natl. Acad. Sci. USA 84, 744–748) which contains sequences needed for polyadenylation (An et al., 1989, Plant Cell 1, 115–122) using restriction sites Nco I and EcoR I resulting in pMOG1367. The entire chimeric gene flanked by restriction sites EcoR I and Hind III was then transferred to pMOG800 (for description of this plasmid see for example WO 97/42326) digested with EcoR I and Hind III.

The resulting binary vector pMOG1368 was introduced in *Agrobacterium tumefaciens* strain EHA105 for transformation of target crops potato and tomato, strain MOG101 for transformation of tobacco and *Arabidopsis thaliana* and strain MOG301 for transformation of *Brassica napus*.

EXAMPLE 9

Transformation of pMOG1368 to Potato cv Kardal pMOG 1368 was transformed to essentially as described by Hoekema et al. (Hoekema, A. et al., Bio/Technology 7, 273–278, 1989). In short, potatoes (*Solanum tuberosum* cv. Kardal) were transformed with the Agrobacterium strain EHA 105 pMOG 1368. The basic culture medium was MS30R3 medium consisting of MS salts (Murashige and Skoog (1962) Physiol. Plant. 14, 473), R3 vitamins (Ooms et al. (1987) Theor. Appl. Genet. 73, 744), 30 g/l sucrose, 0.5 g/l MES with final pH 5.8 (adjusted with KOH) solidified when necessary with 8 g/l Daichin agar. Tubers of *Solanum tuberosum* cv. Kardal were peeled and surface sterilized by burning them in 96% ethanol for 5 seconds. The flames were extinguished in sterile water and cut slices of approximately 2 mm thickness. Disks were cut with a bore from the vascular tissue and incubated for 20 minutes in MS30R3 medium containing 1–5×10⁸ bacteria/ml of Agrobacterium EHA 105 containing the binary vector. The tuber discs were washed with MS30R3 medium and transferred to solidified postculture medium (PM). PM consisted of M30R3 medium supplemented with 3.5 mg/l zeatin riboside and 0.03 mg/l indole acetic acid (IAA). After two days, discs were transferred to fresh PM medium with 200 mg/l cefotaxim and 100 mg/l vancomycin. Three days later, the tuber discs were transferred to shoot induction medium (SIM) which consisted of PM medium with 250 mg/l carbenicillin and 100 mg/l kanamycin. After 4–8 weeks, shoots emerging from the discs were excised and placed on rooting medium (MS30R3-medium with 100 mg/l cefotaxim, 50 mg/l vancomycin and 50 mg/l kanamycin). The shoots were propagated axenically by meristem cuttings.

EXAMPLE 10

Testing of Promoter Function in Transgenic Potato Plants

Transgenic potato plants harbouring the pMOG1368 ms59 promoter-GUS construct were grown in tubes in vitro and assayed for expression of the GUS gene. For this purpose leaf, stem and root samples were taken and stained (results in table 5). GUS expression levels were determined visually, on a scale of 0 to 5, where 0 is no detectable expression and 5 is the highest level of GUS we have observed in leaves of a transgenic plant, of a rare tobacco 355-GUS-transgenic (line 96306). Samples from leaves of this plant were included in all experiments for internal reference.

TABLE 5

Expression of the GUS gene driven by the ms59 promoter in leaves, stems and roots of small in vitro plantlets.

| Plant number | Leaf | Stem | Root |
| --- | --- | --- | --- |
| 1368-1 | 0 | 0 | 0 |
| 1368-2 | 0 | 0 | 0 |
| 1368-3 | 0 | 0 | 0 |
| 1368-4 | 0 | 0 | 0 |
| 1368-5 | 0 | 0 | 0 |
| 1368-6 | 0 | 0 | 0 |
| 1368-7 | 0 | 0 | 0 |
| 1368-8 | 0 | 0 | 0 |
| 1368-9 | 0 | 0 | 0 |
| 1368-10 | 0 | 0 | 0 |
| 1368-11 | 0 | 0 | 0 |
| 1368-12 | 0 | 0 | 1 |
| 1368-13 | 0 | 0 | 0 |
| 1368-14 | 0 | 0 | 0 |
| 1368-15 | 0 | 0 | 0 |
| 1368-16 | 0 | 0 | 0 |
| 1368-17 | 0 | 0 | 0 |
| 1368-18 | 0 | 0 | 1 |
| 1368-19 | 0 | 0 | 0 |
| 1368-20 | 0 | 0 | 0 |
| 1368-21 | 0 | 0 | 0 |
| 1368-22 | 0 | 0 | 0 |
| 1368-23 | 0 | 0 | 0 |
| 1368-24 | 0 | 1 | 0 |
| 1368-25 | 0 | 0 | 0 |
| 1368-26 | 0 | 0 | 0 |
| 1368-27 | 0 | 0 | 0 |
| 1368-28 | 0 | 0 | 0 |
| 1368-29 | 0 | 0 | 0 |
| 1368-30 | 0 | 0 | 0 |

A selection of in vitro plantlets of the same age were infected with the potato late blight causing fungus *Phytophthora infestans*. Small droplets of water containing a high concentration of fungal spores were applied on the leaf surface. The infection was left to proceed at room temperature for 96 hours. Leaves which showed disease symptoms were removed from the plantlets and stained for expression of the GUS gene by histochemical GUS analysis (Goddijn et al., The Plant Journal (1993) 4(5): 863–873). Expression was monitored in the lesion resulting from the fungal infection, in the primary zone (the area just around the site of infection) and in the uninfected part of the leaf (background).

TABLE 6

Expression of the GUS gene driven by the ms59 promoter in leaves of potato in vitro plantlets infected by *P. infestans*

| Plant number | before infection | lesion | primary zone | background |
| --- | --- | --- | --- | --- |
| 1368-1 | 0 | 0 | 0 | 0 |
| 1368-3 | 0 | 0 | 0 | 0 |
| 1368-4 | 0 | 0 | 1 | 0 |
| 13E8-5 | 0 | 0 | 1 | 0 |
| 1368-6 | 0 | 0 | 0 | 0 |

TABLE 6-continued

Expression of the GUS gene driven by the ms59 promoter in leaves of potato in vitro plantlets infected by *P. infestans*

| Plant number | before infection | lesion | primary zone | background |
|---|---|---|---|---|
| 1368-7 | 0 | 0 | 0 | 0 |
| 1368-8 | 0 | 0 | 0 | 0 |
| 1368-9 | 0 | 0 | 1 | 0 |

Promoter performance was also tested in the leaves of full grown potato plants before and after infection with *P. infestans*. Before inoculation leaves were detached and stained for expression of GUS. The plants were then sprayed with a spore suspension of $5 \times 10^5$ spores/ml and the infection was allowed to develop for 4 days (96 hours). Again leaves were detached and stained for the expression of GUS. The results are listed in table 7. Expression was monitored in the lesion, primary zone and the background area.

TABLE 7

Expression of the GUS gene driven by the ms59 promoter in leaves of transgenic potato plants before and after infection with *P. infestans*.

| Plant number | before infection | lesion | primary zone | background |
|---|---|---|---|---|
| 1368-1 | 0 | 0 | 0 | 1 |
| 1368-2 | 0 | 0 | 0 | 1 |
| 1365-3 | 0 | 0 | 0 | 0 |
| 1368-4 | 0 | 0 | 0 | 0 |
| 1368-5 | 0 | 0 | 0 | 0 |
| 1368-6 | 0 | 0 | 0 | 0 |
| 1368-7 | 0 | 0 | 0 | 0 |
| 1368-9 | 0 | 0 | 0 | 0 |
| 1368-10 | 0 | 0 | 0 | 0 |
| 1368-11 | 0 | 0 | 0 | 0 |
| 1368-12 | 2 | 0 | 2 | 2 |
| 1368-13 | 0 | 0 | 0 | 0 |
| 1368-14 | 0 | 0 | 0 | 0 |
| 1368-15 | 0 | 0 | 0 | 0 |
| 1368-16 | 0 | 0 | 0 | 0 |
| 1368-17 | 0 | 0 | 0 | 0 |
| 1368-18 | 0 | 0 | 2 | 0 |
| 1368-19 | 0 | 0 | 0 | 0 |
| 1368-20 | 0 | 0 | 0 | 0 |
| 1368-21 | 0 | 0 | 0 | 0 |
| 1368-22 | 0 | 0 | 0 | 0 |
| 1368-23 | 0 | 0 | 0 | 0 |
| 1366-24 | 0 | 0 | 0 | 0 |
| 136B-25 | 0 | 0 | 0 | 0 |
| 1368-26 | 0 | 0 | 3 | 0 |

The results showed that the ms59 promoter responds to fungal infection. The level of induced expression is rather low and may be below the detection level in some cases. This would explain the low frequency of detectable inducible GUS expression.

What is claimed is:

1. An isolated DNA sequence which in nature drives expression of a plant gene coding for hexose oxidase, wherein said isolated DNA sequence promotes transcription of an associated DNA sequence when re-introduced into a plant, wherein said isolated DNA sequence is obtained from *Helianrhus annuus*, and wherein said isolated DNA sequence comprises the nucleotide sequence from 1 to 1889 of the sequence depicted in SEQ ID NO:15.

2. A chimeric DNA sequence comprising in the direction of transcription:
   (a) an isolated DNA sequence according to claim 1; and
   (b) a DNA sequence to be expressed under the transcriptional control thereof and which, in nature, is not under transcriptional control of said isolated DNA sequence.

3. A replicon comprising in the direction of transcription a DNA sequence according claim 1 and at least one recognition site for a restriction endonuclease for insertion of a DNA sequence to be expressed under the control of said DNA sequence.

4. A chimeric DNA sequence according to claim 2, wherein the DNA sequence to be expressed causes the production of an antipathogenic protein.

5. A chimeric DNA sequence according to claim 4, wherein said antipathogenic protein is selected from the group consisting of chitinase, glucanase, osmotin, magainins, lectins, saccharide oxidase, oxalate oxidase, toxin from *Bacillus thuringiensis*, antifungal protein isolated from *Mirabilis jalapa*, antifungal protein isolated from Amaranthus, antifungal protein isolated from Raphanus, antifungal protein isolated from Brassica, antifungal protein isolated from Sinapis, antifungal protein isolated from Arabidopsis, Dahlia, antifungal protein isolated from Cnicus, antifungal protein isolated from Lathyrus, antifungal protein isolated from Clitoria, antifungal protein isolated from Allium seeds, antifungal protein isolated from Aralia, antifungal protein isolated from Impatiens, albumin-type protein, thionine, napin, barley trypsin inhibitor, cereal gliadin and wheat-alpha-amylase.

6. A chimeric DNA sequence according to claim 2, wherein said DNA sequence to be expressed induces production of a protein that induces a hypersensitive response, wherein said protein is selected from the group consisting of Cf protein from tomato, Bs3 protein from tomato, Pto protein from tomato, Rpm1 from *Arabidopsis thaliana*, Rps2 from Arabidopsis thaliana, N-protein from tobacco, avr proteins from Cladosporiumfulvum, harpins from Erwinia, elicitor proteins from Pseudomonas, and elicitor proteins from Xanthomonas.

7. A replicon comprising a chimeric DNA sequence according to claim 2.

8. A microorganism containing a replicon according to claim 7.

9. A plant cell having incorporated into its genome a chimeric DNA sequence according to claim 2.

10. A method for generating a transgenic plant comprising:
    (a) constructing a chimeric DNA sequence according to claim 2,
    (b) transforming said chimeric DNA sequence into a recipient plant cell; and
    (c) regenerating said plant cell into a mature plant, wherein said mature plant is a transgenic plant comprising said chimeric DNA sequence.

11. A plant essentially consisting of cells according to claim 9.

12. A plant according to claim 11 which is a dicotyledonous plant.

13. A part of a plant having inserted in its genome at least an additional copy of a chimeric DNA sequence, said part of a plant selected from seeds, flowers, tubers, roots, leaves, fruits, pollen and wood, obtained from a plant according to claim 11.

* * * * *

UNITED STATES PATENT AND TRADEMARK OFFICE
CERTIFICATE OF CORRECTION

PATENT NO.    : 6,465,636 B1
DATED         : October 15, 2002
INVENTOR(S)   : Maarten Hendrik Stuiver et al.

Page 1 of 1

It is certified that error appears in the above-identified patent and that said Letters Patent is hereby corrected as shown below:

Column 35,
Line 37, please delete the "r" in "*Helianhus*".
Line 60, please delete "Amaranthus" and replace with -- *Amaranthus* -- and delete "Raphanus" and replace with -- *Raphanus* --.
Line 61, please delete "Brassica" and replace with -- *Brassica* --.
Line 62, please delete "Sinapis" and replace with -- *Sinapis* --.
Line 63, please delete "Arabidopsis" and replace with -- *Arabidopsis* --, and delete "Dahlia" and replace with -- *Dahlia* --.
Line 64, please delete "Cnicus" and replace with -- *Cnicus* --, and delete "Lathyrus" and replace with -- *Lathyrus* --.
Line 65, please delete "Clitoria" and replace with -- *Clitoria* --.
Line 66, please delete "Allium" and replace with -- *Allium* --, and delete "Aralia" and replace with -- *Aralia* --.
Line 67, please delete "Impatiens" and replace with -- *Impatiens* --.

Column 36,
Line 39, please delete "Arabidopsis thaliana" and replace with -- *Arabidopsis thaliana* --.
Line 40, please delete "Cladosporiumfulvim" and replace with -- *Cladosporium fulvim* --.
Line 41, please delete "Pseudomonas" and replace with -- *Pseudomonas* --.
Line 42, please delete "Xanthomonas" and replace with -- *Xanthomonas* --.

Signed and Sealed this

Eighteenth Day of February, 2003

JAMES E. ROGAN
*Director of the United States Patent and Trademark Office*

SEQUENCE LISTING

```
<160> NUMBER OF SEQ ID NOS: 18

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 1
gttccggagg ttgtgaccgt gggatgtgct gcaaggcg                           38

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 2
ctggggaagc ccgtgtagta aagccccgc gcgttggccg attc                    44

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 3
```

-continued

```
ctggggaagc ccgtgtagta aagc                                              24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 4
gttccggagg ttgtgaccgt g                                                 21

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 5
ccatgggctc aaactggagc cggccgggag cagacaagcc cg                          42

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 6
cgagacgtca acagtcggga cccactcatt aggcacccca ggc                         43

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 7
ccatgggctc aaactggagc cg                                                22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 8
cgagacgtca acagtcggga cc                                                22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
caggcagctg tggtttgtgg c                                                 21

<210> SEQ ID NO 10
<211> LENGTH: 25
<212> TYPE: DNA
<213> ORGANISM: Artificial Sequence
```

```
<220> FEATURE:
<223> OTHER INFORMATION: Description of Artificial Sequence:primer

<400> SEQUENCE: 10
cgggaagttg cagaagattg ggttg                                          25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 11
acgtagatat cgaacaagaa accgc                                          25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 12
gagcaagaga agaaggagac                                                20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 13
gcaagcttta tagtttacga tcc                                            23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 14
ttgccatggt gcatggttta gcg                                            23

<210> SEQ ID NO 15
<211> LENGTH: 3680
<212> TYPE: DNA
<213> ORGANISM: Helianthus annuus
<220> FEATURE:
<221> NAME/KEY: promoter
<222> LOCATION: (1)..(1889)
<221> NAME/KEY: CDS
<222> LOCATION: (1890)..(3503)

<400> SEQUENCE: 15
aagctttata gtttacgatc caaggttcga tgtgttagtt ccaacaacgt tggagtcgaa     60 gttctttta ggagtttttt ttttttttc aaactagtgt tggtagaaaa agtatttact     120
aaagtggtgt tccttgaaaa atatttacca aaataatgtt tttgtctcct ttctcatctt    180
aatgaatata aactaaatta ctaattctat tatttatttc tgttaacact ttatttacta    240 ttattttta gaaacccaat aaaactaaat tagtaatttt attatttatt atattgacac     300
tttattttct ttttgaaact cagacttgag gttctccatt atgtcaccta atattatctt    360
```

-continued

```
atctaataat ttatacatga ttaacataat ttactcaatt tataattata tctaaattca      420
ctttaacata tattttgtta tttttagttg taacaataaa agtgttaagt tagttagtta      480 taaaaaggt cagaaagtaa aatagtttag tatgtttgtt aatataagat tacaaaaaag       540 taaaaaagt aagccataaa aataaaattt gggagttcgt tttctatgac ttgacaacac       600
tttaaagtag tttaatcgat caaaaataca tgatatatta tttatctagt aaaaaataaa      660
aataaaacaa tattagcgta gataagagtg ataaataatt tttttattaa ataattgaaa     720
tttttaaaaa agatcatttt ctaaaaatcc gtagcgagta aagttatgat gtttgtctaa      780
cttttttatg tttcttattt catactgttt aatatataaa agataagga gttggtaaaa      840 caaaatataa agagttggtt aaaggtaaaa aaaaaaaaaa aaaaaaaaaa aaaaaaaacc     900
tataatggat tgattggagc aaaacaaaat attttattga ttgaataaaa aaatataaca     960
aaaacataat gaataagaag tattacatta cattggcttt aaaaaataat caagtattaa     1020
tagaaataaa taatgaatta ctaaattagt ttttattcaa tgagataaga atagagaaaa     1080
aaacaccatt ttagtaaata cttttgaaaa acaccatttg atgaatattt tttttcacca     1140
tcactacttt aggaaaaaaa aaaaaaactc ttctttttag tctaatattg agttttttaaa    1200 atacttatca tacttattag acaaaacaat catttttagag taaccttccc ctatacccta    1260
aagtatatat agacgattct aattaaggta ccatataata cagtttaaaa tgatttcatt    1320
aattatccaa aattttttact tttgtttaat tcttttttggt tcgtatgtac ttgtataatt    1380
caaagtcttc gtggatttaa attactttga atcaaaaata tgtttgaaat agctgacatg     1440 tgtattttt caaattgtac ataaatatac gcaaactcga aattgaaaag ttgaaagaaa     1500
acgtgtttca tttttttgaaa agtaggcctt atgcaacttg ctattttctc gactatccat    1560
gtttatctcc agattttaa tttatttgtg tttctttata tctttaacaa gttacaagca     1620
tatggaatta tgtacctatg cactttcact taaaatttat gtcttgttag gagaaattat     1680
tttaaaatca atgttctaat atataaaaat ccaaattaag caatgacact taaaacatat     1740
gaccaatgac acgatatgat gagtacgtac ccaatatgaa ttttcaactt tgattagtta     1800
tatttggtat gtcattttg aaggtcaaac attacgactt tcaattgcct ataaattgca     1860
tgcatcaagc aaacgctaaa ccatgcaaa atg gca aat atc aca tct tct ttc       1913
                                   Met Ala Asn Ile Thr Ser Ser Phe
                                   1               5 aac atg caa act tcc att ctt act ctc ctt ctt ctc ttg ctc tca acc       1961
Asn Met Gln Thr Ser Ile Leu Thr Leu Leu Leu Leu Leu Leu Ser Thr
    10              15                  20 caa tct tct gca act tcc cgt tcc att aca gat cgc ttc att caa tgt       2009
Gln Ser Ser Ala Thr Ser Arg Ser Ile Thr Asp Arg Phe Ile Gln Cys
25              30                  35                  40 tta cac gac cgg gcc gac cct tca ttt ccg ata acc gga gag gtt tac       2057
Leu His Asp Arg Ala Asp Pro Ser Phe Pro Ile Thr Gly Glu Val Tyr
                45                  50                  55 act ccc gga aac tca tct ttt cct acc gtc ttg caa aac tac atc cga       2105
Thr Pro Gly Asn Ser Ser Phe Pro Thr Val Leu Gln Asn Tyr Ile Arg
            60                  65                  70 aac ctt cgg ttc aat gaa act acc aca cca aaa ccc ttt tta atc atc       2153
Asn Leu Arg Phe Asn Glu Thr Thr Thr Pro Lys Pro Phe Leu Ile Ile
        75                  80                  85 aca gcc gaa cat gtt tcc cac att cag gca gct gtg gtt tgt ggc aaa       2201
Thr Ala Glu His Val Ser His Ile Gln Ala Ala Val Val Cys Gly Lys
    90                  95                  100
```

-continued

| | | |
|---|---|---|
| caa aac cgg ttg cta ctg aaa acc aga agc ggt ggt cat gat tat gaa<br>Gln Asn Arg Leu Leu Leu Lys Thr Arg Ser Gly Gly His Asp Tyr Glu<br>105                        110                        115                        120 | | 2249 |
| ggt ctt tcc tac ctt aca aac aca aac caa ccc ttc ttc att gtg gac<br>Gly Leu Ser Tyr Leu Thr Asn Thr Asn Gln Pro Phe Phe Ile Val Asp<br>                    125                        130                        135 | | 2297 |
| atg ttc aat tta agg tcc ata aac gta gat atc gaa caa gaa acc gca<br>Met Phe Asn Leu Arg Ser Ile Asn Val Asp Ile Glu Gln Glu Thr Ala<br>140                        145                        150 | | 2345 |
| tgg gtc caa gcc ggt gcg act ctt ggt gaa gtg tac tat cga ata gcg<br>Trp Val Gln Ala Gly Ala Thr Leu Gly Glu Val Tyr Tyr Arg Ile Ala<br>               155                        160                        165 | | 2393 |
| gag aaa agt aac aag cat ggt ttt ccg gca ggg gtt tgt cca acg gtt<br>Glu Lys Ser Asn Lys His Gly Phe Pro Ala Gly Val Cys Pro Thr Val<br>170                        175                        180 | | 2441 |
| ggc gtt ggt ggg cat ttt agt ggt ggt ggg tat ggt aat ttg atg aga<br>Gly Val Gly Gly His Phe Ser Gly Gly Gly Tyr Gly Asn Leu Met Arg<br>185                        190                        195                        200 | | 2489 |
| aaa tat ggt ttg tcg gtt gat aat att gtt gat gct caa ata ata gat<br>Lys Tyr Gly Leu Ser Val Asp Asn Ile Val Asp Ala Gln Ile Ile Asp<br>                    205                        210                        215 | | 2537 |
| gtg aat ggc aag ctt ttg gat cga aag agt atg ggt gag gat ttg ttt<br>Val Asn Gly Lys Leu Leu Asp Arg Lys Ser Met Gly Glu Asp Leu Phe<br>220                        225                        230 | | 2585 |
| tgg gcg atc acc ggc ggt ggt gtt agt ttt ggt gtg gtt cta gcc<br>Trp Ala Ile Thr Gly Gly Gly Val Ser Phe Gly Val Val Leu Ala<br>235                        240                        245 | | 2633 |
| tac aaa atc aaa cta gtt cgt gtt ccg gag gtt gtg acc gtg ttt acc<br>Tyr Lys Ile Lys Leu Val Arg Val Pro Glu Val Val Thr Val Phe Thr<br>250                        255                        260 | | 2681 |
| att gaa aga aga gag gaa caa aac ctc agc acc atc gcg gaa cga tgg<br>Ile Glu Arg Arg Glu Glu Gln Asn Leu Ser Thr Ile Ala Glu Arg Trp<br>265                        270                        275                        280 | | 2729 |
| gta caa gtt gct gat aag cta gat aga gat ctt ttc ctt cga atg acc<br>Val Gln Val Ala Asp Lys Leu Asp Arg Asp Leu Phe Leu Arg Met Thr<br>                    285                        290                        295 | | 2777 |
| ttt agt gtc ata aac gat acc aac ggt gga aag aca gtc cgt gct atc<br>Phe Ser Val Ile Asn Asp Thr Asn Gly Gly Lys Thr Val Arg Ala Ile<br>                    300                        305                        310 | | 2825 |
| ttt cca acg ttg tac ctt gga aac tcg agg aat ctt gtt aca ctt ttg<br>Phe Pro Thr Leu Tyr Leu Gly Asn Ser Arg Asn Leu Val Thr Leu Leu<br>               315                        320                        325 | | 2873 |
| aat aaa gat ttc ccc gag tta ggg ttg caa gaa tcg gat tgt act gaa<br>Asn Lys Asp Phe Pro Glu Leu Gly Leu Gln Glu Ser Asp Cys Thr Glu<br>330                        335                        340 | | 2921 |
| atg agt tgg gtt gag tct gtg ctt tac tac acg ggc ttc ccc agt ggt<br>Met Ser Trp Val Glu Ser Val Leu Tyr Tyr Thr Gly Phe Pro Ser Gly<br>345                        350                        355                        360 | | 2969 |
| act cca acc acg gcg ctc tta agc cgt act cct caa aga ctc aac cca<br>Thr Pro Thr Thr Ala Leu Leu Ser Arg Thr Pro Gln Arg Leu Asn Pro<br>                    365                        370                        375 | | 3017 |
| ttc aag atc aaa tcc gat tat gtg caa aat cct att tct aaa cga cag<br>Phe Lys Ile Lys Ser Asp Tyr Val Gln Asn Pro Ile Ser Lys Arg Gln<br>               380                        385                        390 | | 3065 |
| ttc gag ttc atc ttc gaa agg ctg aaa gaa ctt gaa aac caa atg ttg<br>Phe Glu Phe Ile Phe Glu Arg Leu Lys Glu Leu Glu Asn Gln Met Leu<br>395                        400                        405 | | 3113 |
| gct ttc aac cca tat ggt ggt aga atg agt gaa ata tcc gaa ttc gca<br>Ala Phe Asn Pro Tyr Gly Gly Arg Met Ser Glu Ile Ser Glu Phe Ala<br>          410                        415                        420 | | 3161 |

| | | |
|---|---|---|
| aag cct ttc cca cat aga tcg ggt aac ata gcg aaa att caa tac gaa<br>Lys Pro Phe Pro His Arg Ser Gly Asn Ile Ala Lys Ile Gln Tyr Glu<br>425                           430                             435                         440 | 3209 |
| gta aac tgg gag gat ctt agc gat gaa gcc gaa aat cgt tac ttg aat<br>Val Asn Trp Glu Asp Leu Ser Asp Glu Ala Glu Asn Arg Tyr Leu Asn<br>                               445                            450                         455 | 3257 |
| ttc aca agg ctg atg tat gat tac atg acc cca ttt gtg tcg aaa aac<br>Phe Thr Arg Leu Met Tyr Asp Tyr Met Thr Pro Phe Val Ser Lys Asn<br>           460                           465                           470 | 3305 |
| cct aga aaa gca ttt ttg aac tat agg gat ttg gat att ggt atc aac<br>Pro Arg Lys Ala Phe Leu Asn Tyr Arg Asp Leu Asp Ile Gly Ile Asn<br>475                           480                           485 | 3353 |
| agc cat ggc agg aat gct tat act gaa gga atg gtt tat ggg cac aag<br>Ser His Gly Arg Asn Ala Tyr Thr Glu Gly Met Val Tyr Gly His Lys<br>           490                           495                         500 | 3401 |
| tat ttc aaa gag aca aat tac aag agg cta gta agt gtg aag act aaa<br>Tyr Phe Lys Glu Thr Asn Tyr Lys Arg Leu Val Ser Val Lys Thr Lys<br>505                         510                             515                        520 | 3449 |
| gtt gat cct gac aac ttc ttt agg aat gag caa agc atc cca act ttg<br>Val Asp Pro Asp Asn Phe Phe Arg Asn Glu Gln Ser Ile Pro Thr Leu<br>                             525                            530                        535 | 3497 |
| tca tct tgaagaacgt acatatataa ataaataacct ttgtgcatgg tattttcagg<br>Ser Ser | 3553 |
| gtgttaaagt gatattcaga tatttatgat agaattttga cttgtatttt atacaatcaa | 3613 |
| aattgtatgg ttctccgaat ttctctttttt aattctgaaa aatacatatt agtattgtca | 3673 |
| aaaaaaa | 3680 |

<210> SEQ ID NO 16
<211> LENGTH: 538
<212> TYPE: PRT
<213> ORGANISM: Helianthus annuus

<400> SEQUENCE: 16

Met Ala Asn Ile Thr Ser Ser Phe Asn Met Gln Thr Ser Ile Leu Thr
1               5                   10                  15

Leu Leu Leu Leu Leu Leu Ser Thr Gln Ser Ser Ala Thr Ser Arg Ser
            20                  25                  30

Ile Thr Asp Arg Phe Ile Gln Cys Leu His Asp Arg Ala Asp Pro Ser
        35                  40                  45

Phe Pro Ile Thr Gly Glu Val Tyr Thr Pro Gly Asn Ser Ser Phe Pro
    50                  55                  60

Thr Val Leu Gln Asn Tyr Ile Arg Asn Leu Arg Phe Asn Glu Thr Thr
65                  70                  75                  80

Thr Pro Lys Pro Phe Leu Ile Ile Thr Ala Glu His Val Ser His Ile
                85                  90                  95

Gln Ala Ala Val Val Cys Gly Lys Gln Asn Arg Leu Leu Leu Lys Thr
            100                 105                 110

Arg Ser Gly Gly His Asp Tyr Glu Gly Leu Ser Tyr Leu Thr Asn Thr
        115                 120                 125

Asn Gln Pro Phe Phe Ile Val Asp Met Phe Asn Leu Arg Ser Ile Asn
    130                 135                 140

Val Asp Ile Glu Gln Glu Thr Ala Trp Val Gln Ala Gly Ala Thr Leu
145                 150                 155                 160

Gly Glu Val Tyr Tyr Arg Ile Ala Glu Lys Ser Asn Lys His Gly Phe
                165                 170                 175

```
Pro Ala Gly Val Cys Pro Thr Val Gly Gly His Phe Ser Gly
            180                 185                 190

Gly Gly Tyr Gly Asn Leu Met Arg Lys Tyr Gly Leu Ser Val Asp Asn
        195                 200                 205

Ile Val Asp Ala Gln Ile Ile Asp Val Asn Gly Lys Leu Leu Asp Arg
        210                 215                 220

Lys Ser Met Gly Glu Asp Leu Phe Trp Ala Ile Thr Gly Gly Gly
225                 230                 235                 240

Val Ser Phe Gly Val Val Leu Ala Tyr Lys Ile Lys Leu Val Arg Val
                245                 250                 255

Pro Glu Val Val Thr Val Phe Thr Ile Glu Arg Arg Glu Glu Gln Asn
                260                 265                 270

Leu Ser Thr Ile Ala Glu Arg Trp Val Gln Val Ala Asp Lys Leu Asp
            275                 280                 285

Arg Asp Leu Phe Leu Arg Met Thr Phe Ser Val Ile Asn Asp Thr Asn
        290                 295                 300

Gly Gly Lys Thr Val Arg Ala Ile Phe Pro Thr Leu Tyr Leu Gly Asn
305                 310                 315                 320

Ser Arg Asn Leu Val Thr Leu Leu Asn Lys Asp Phe Pro Glu Leu Gly
                325                 330                 335

Leu Gln Glu Ser Asp Cys Thr Glu Met Ser Trp Val Glu Ser Val Leu
            340                 345                 350

Tyr Tyr Thr Gly Phe Pro Ser Gly Thr Pro Thr Thr Ala Leu Leu Ser
        355                 360                 365

Arg Thr Pro Gln Arg Leu Asn Pro Phe Lys Ile Lys Ser Asp Tyr Val
    370                 375                 380

Gln Asn Pro Ile Ser Lys Arg Gln Phe Glu Phe Ile Phe Glu Arg Leu
385                 390                 395                 400

Lys Glu Leu Glu Asn Gln Met Leu Ala Phe Asn Pro Tyr Gly Gly Arg
                405                 410                 415

Met Ser Glu Ile Ser Glu Phe Ala Lys Pro Phe Pro His Arg Ser Gly
            420                 425                 430

Asn Ile Ala Lys Ile Gln Tyr Glu Val Asn Trp Glu Asp Leu Ser Asp
        435                 440                 445

Glu Ala Glu Asn Arg Tyr Leu Asn Phe Thr Arg Leu Met Tyr Asp Tyr
    450                 455                 460

Met Thr Pro Phe Val Ser Lys Asn Pro Arg Lys Ala Phe Leu Asn Tyr
465                 470                 475                 480

Arg Asp Leu Asp Ile Gly Ile Asn Ser His Gly Arg Asn Ala Tyr Thr
                485                 490                 495

Glu Gly Met Val Tyr Gly His Lys Tyr Phe Lys Glu Thr Asn Tyr Lys
            500                 505                 510

Arg Leu Val Ser Val Lys Thr Lys Val Asp Pro Asp Asn Phe Phe Arg
        515                 520                 525

Asn Glu Gln Ser Ile Pro Thr Leu Ser Ser
    530                 535     538

<210> SEQ ID NO 17
<211> LENGTH: 1981
<212> TYPE: DNA
<213> ORGANISM: Lactuca sativa
<220> FEATURE:
<221> NAME/KEY: CDS
<222> LOCATION: (7)..(1626)
<221> NAME/KEY: unsure
<222> LOCATION: (372)
```

-continued

```
<223> OTHER INFORMATION: replace (372, "g")
<221> NAME/KEY: unsure
<222> LOCATION: (379)
<223> OTHER INFORMATION: replace (379, "g")
<221> NAME/KEY: unsure
<222> LOCATION: (786)
<223> OTHER INFORMATION: replace (786, "t")
<221> NAME/KEY: unsure
<222> LOCATION: (1105)..(1106)
<223> OTHER INFORMATION: replace (1105..1106, "ga" or "gg" or "aa")

<400> SEQUENCE: 17 acaaaa atg gca att acc tat tct ttc aac ttc aaa tct tat att ttt      48
       Met Ala Ile Thr Tyr Ser Phe Asn Phe Lys Ser Tyr Ile Phe
        1               5                  10 cct ctc ctc ctt gtc ttg ctc tct acc cat tca tca gcg act tca act     96
Pro Leu Leu Leu Val Leu Leu Ser Thr His Ser Ser Ala Thr Ser Thr
 15              20                  25                  30 tcc att ata gat cgc ttc acc caa tgt cta aac aac cga gct gac cct    144
Ser Ile Ile Asp Arg Phe Thr Gln Cys Leu Asn Asn Arg Ala Asp Pro
             35                  40                  45 tct ttc ccg ctc agt gga caa ctt tac act ccc gat aac tcc tct ttt    192
Ser Phe Pro Leu Ser Gly Gln Leu Tyr Thr Pro Asp Asn Ser Ser Phe
         50                  55                  60 cca tcc gtc ttg caa gct tac atc cgg aac ctc cga ttc aat gaa tcc    240
Pro Ser Val Leu Gln Ala Tyr Ile Arg Asn Leu Arg Phe Asn Glu Ser
         65                  70                  75 acg act ccc aaa ccc atc tta atc atc acc gcc tta cac cct tca cac    288
Thr Thr Pro Lys Pro Ile Leu Ile Ile Thr Ala Leu His Pro Ser His
 80                  85                  90 att caa gca gct gtt gtg tgc gcc aaa aca cac cgc ctg cta atg aaa    336
Ile Gln Ala Ala Val Val Cys Ala Lys Thr His Arg Leu Leu Met Lys
 95                 100                 105                 110 acc aga agc gga ggc cat gat tat gag ggg ctt tcc tat gtg acc aat    384
Thr Arg Ser Gly Gly His Asp Tyr Glu Gly Leu Ser Tyr Val Thr Asn
                 115                 120                 125 tcg aac caa ccc ttt ttt gtt gtt gac atg ttc aac tta cgc tcc ata    432
Ser Asn Gln Pro Phe Phe Val Val Asp Met Phe Asn Leu Arg Ser Ile
             130                 135                 140 aac gtg agt att gaa gat gaa act gca tgg gtc caa gct ggt gcg act    480
Asn Val Ser Ile Glu Asp Glu Thr Ala Trp Val Gln Ala Gly Ala Thr
145                 150                 155 ctt ggt gaa gtc tac tac cga ata gca gag aaa agc aac agt cat gct    528
Leu Gly Glu Val Tyr Tyr Arg Ile Ala Glu Lys Ser Asn Ser His Ala
160                 165                 170 ttt ccg gct ggc gtt tgc cct act gtt gga gtt ggt ggc cat ttt agt    576
Phe Pro Ala Gly Val Cys Pro Thr Val Gly Val Gly Gly His Phe Ser
175                 180                 185                 190 ggt ggt ggt tat ggt aac ttg atg gga aaa tac ggc ctt tct gtt gac    624
Gly Gly Gly Tyr Gly Asn Leu Met Gly Lys Tyr Gly Leu Ser Val Asp
                 195                 200                 205 aat att gtc gat gct cag tta atc gat gtg aat ggt aaa ctt ctg aat    672
Asn Ile Val Asp Ala Gln Leu Ile Asp Val Asn Gly Lys Leu Leu Asn
             210                 215                 220 cgg aaa tca atg ggt gaa gat ctt ttt tgg gcc atc aca ggt ggt ggt    720
Arg Lys Ser Met Gly Glu Asp Leu Phe Trp Ala Ile Thr Gly Gly Gly
         225                 230                 235 ggt gtc agc ttt ggt gtg gtt gta gcg tac aag atc aaa ctg gtt cgt    768
Gly Val Ser Phe Gly Val Val Val Ala Tyr Lys Ile Lys Leu Val Arg
240                 245                 250 gtt cct acc act gtg acc gtt ttt aac gta caa aga aca tcc gag cag    816
Val Pro Thr Thr Val Thr Val Phe Asn Val Gln Arg Thr Ser Glu Gln
```

```
      255                   260                   265                   270
aac cta agc acc ata gcc cac cga tgg ata caa gtt gcg gat aag ctc         864
Asn Leu Ser Thr Ile Ala His Arg Trp Ile Gln Val Ala Asp Lys Leu
            275                   280                   285 gat aat gac ctt ttc ctt cga atg acc ttt aac gtg ata aac aac aca         912
Asp Asn Asp Leu Phe Leu Arg Met Thr Phe Asn Val Ile Asn Asn Thr
            290                   295                   300 aat ggc gaa aag acg ata cgt ggt ttg ttt cca aca ctg tac ctc gga         960
Asn Gly Glu Lys Thr Ile Arg Gly Leu Phe Pro Thr Leu Tyr Leu Gly
            305                   310                   315 aac tct acc gct ctt gtt gcc ctc ctg aac aag gat ttc cct gaa tta        1008
Asn Ser Thr Ala Leu Val Ala Leu Leu Asn Lys Asp Phe Pro Glu Leu
            320                   325                   330 ggt gta gaa att tca gat tgt att gaa atg agt tgg atc gag tct gtt        1056
Gly Val Glu Ile Ser Asp Cys Ile Glu Met Ser Trp Ile Glu Ser Val
335                   340                   345                   350 ctt ttc tac aca aac ttc ccc att ggt act ccg acc act gct ctt cta        1104
Leu Phe Tyr Thr Asn Phe Pro Ile Gly Thr Pro Thr Thr Ala Leu Leu
                355                   360                   365 agc cgt aca cct caa aga cta aac cca ttc aaa atc aaa tct gat tac        1152
Ser Arg Thr Pro Gln Arg Leu Asn Pro Phe Lys Ile Lys Ser Asp Tyr
            370                   375                   380 gta aaa aac act att tcc aaa cag gga ttc gaa tcc ata ttt gaa agg        1200
Val Lys Asn Thr Ile Ser Lys Gln Gly Phe Glu Ser Ile Phe Glu Arg
            385                   390                   395 atg aaa gaa ctc gaa aac caa atg cta gct ttc aac cct tat ggt gga        1248
Met Lys Glu Leu Glu Asn Gln Met Leu Ala Phe Asn Pro Tyr Gly Gly
            400                   405                   410 aga atg agc gaa att tcc gaa ttt gca aag cct ttt ccc cat cga tca        1296
Arg Met Ser Glu Ile Ser Glu Phe Ala Lys Pro Phe Pro His Arg Ser
415                   420                   425                   430 ggg aat ata gcg aag atc caa tac gaa gta aac tgg gat gaa ctt ggc        1344
Gly Asn Ile Ala Lys Ile Gln Tyr Glu Val Asn Trp Asp Glu Leu Gly
                435                   440                   445 gtt gaa gca gcc aat cgg tac ttg aac ttc aca agg gtg atg tat gat        1392
Val Glu Ala Ala Asn Arg Tyr Leu Asn Phe Thr Arg Val Met Tyr Asp
            450                   455                   460 tat atg act ccg ttt gtt tct aag aac ccc agg gaa gca ttt ctg aac        1440
Tyr Met Thr Pro Phe Val Ser Lys Asn Pro Arg Glu Ala Phe Leu Asn
            465                   470                   475 tac agg gat tta gat att ggt gtc aac agt cat ggc aag aat gct tac        1488
Tyr Arg Asp Leu Asp Ile Gly Val Asn Ser His Gly Lys Asn Ala Tyr
480                   485                   490 ggt gaa gga atg gtt tat ggg cac aag tat ttc aaa gag acg aat tat        1536
Gly Glu Gly Met Val Tyr Gly His Lys Tyr Phe Lys Glu Thr Asn Tyr
495                   500                   505                   510 aag agg cta acg atg gtg aag acg agg gtt gat cct agc aat ttt ttt        1584
Lys Arg Leu Thr Met Val Lys Thr Arg Val Asp Pro Ser Asn Phe Phe
                515                   520                   525 agg aat gag caa agt atc cca act ttg tca tct tca tgg aag                1626
Arg Asn Glu Gln Ser Ile Pro Thr Leu Ser Ser Ser Trp Lys
            530                   535                   540 taaattctaa attcacttgt gaaattgaat aaaagtatgg cttttttcaag gtcatggtat     1686 ccagattcag atgatattga tataattttg acttgtattt atacaaacaa aattatatta     1746 tattttttctg aatttagatt ttccattctt tggaaaaata tacgaacatt gatgttgata    1806
tttttaagaa ttatagattt tgaacattgt gaacaatgaa taaaccgagg acttcccttg     1866 ggttttttttt ataagtatgt aatagcatgt ctttaatcaa gataaccgat cattggatgc    1926
```
aatttattat tataaacctt atttaaaaaa aaaaaaaaaa aaaaaaaaaa aaaaa          1981

<210> SEQ ID NO 18
<211> LENGTH: 540
<212> TYPE: PRT
<213> ORGANISM: Lactuca sativa

<400> SEQUENCE: 18

```
Met Ala Ile Thr Tyr Ser Phe Asn Phe Lys Ser Tyr Ile Phe Pro Leu
 1               5                  10                  15

Leu Leu Val Leu Leu Ser Thr His Ser Ser Ala Thr Ser Thr Ser Ile
             20                  25                  30

Ile Asp Arg Phe Thr Gln Cys Leu Asn Asn Arg Ala Asp Pro Ser Phe
         35                  40                  45

Pro Leu Ser Gly Gln Leu Tyr Thr Pro Asp Asn Ser Ser Phe Pro Ser
     50                  55                  60

Val Leu Gln Ala Tyr Ile Arg Asn Leu Arg Phe Asn Glu Ser Thr Thr
 65                  70                  75                  80

Pro Lys Pro Ile Leu Ile Thr Ala Leu His Pro Ser His Ile Gln
                 85                  90                  95

Ala Ala Val Val Cys Ala Lys Thr His Arg Leu Leu Met Lys Thr Arg
            100                 105                 110

Ser Gly Gly His Asp Tyr Glu Gly Leu Ser Tyr Val Thr Asn Ser Asn
        115                 120                 125

Gln Pro Phe Phe Val Val Asp Met Phe Asn Leu Arg Ser Ile Asn Val
    130                 135                 140

Ser Ile Glu Asp Glu Thr Ala Trp Val Gln Ala Gly Ala Thr Leu Gly
145                 150                 155                 160

Glu Val Tyr Tyr Arg Ile Ala Glu Lys Ser Asn Ser His Ala Phe Pro
                165                 170                 175

Ala Gly Val Cys Pro Thr Val Gly Val Gly Gly His Phe Ser Gly Gly
            180                 185                 190

Gly Tyr Gly Asn Leu Met Gly Lys Tyr Gly Leu Ser Val Asp Asn Ile
        195                 200                 205

Val Asp Ala Gln Leu Ile Asp Val Asn Gly Lys Leu Leu Asn Arg Lys
    210                 215                 220

Ser Met Gly Glu Asp Leu Phe Trp Ala Ile Thr Gly Gly Gly Gly Val
225                 230                 235                 240

Ser Phe Gly Val Val Val Ala Tyr Lys Ile Lys Leu Val Arg Val Pro
                245                 250                 255

Thr Thr Val Thr Val Phe Asn Val Gln Arg Thr Ser Glu Gln Asn Leu
            260                 265                 270

Ser Thr Ile Ala His Arg Trp Ile Gln Val Ala Asp Lys Leu Asp Asn
        275                 280                 285

Asp Leu Phe Leu Arg Met Thr Phe Asn Val Ile Asn Asn Thr Asn Gly
    290                 295                 300

Glu Lys Thr Ile Arg Gly Leu Phe Pro Thr Leu Tyr Leu Gly Asn Ser
305                 310                 315                 320

Thr Ala Leu Val Ala Leu Leu Asn Lys Asp Phe Pro Glu Leu Gly Val
                325                 330                 335

Glu Ile Ser Asp Cys Ile Glu Met Ser Trp Ile Glu Ser Val Leu Phe
            340                 345                 350

Tyr Thr Asn Phe Pro Ile Gly Thr Pro Thr Thr Ala Leu Leu Ser Arg
        355                 360                 365
```

-continued

```
Thr Pro Gln Arg Leu Asn Pro Phe Lys Ile Lys Ser Asp Tyr Val Lys
    370                 375                 380

Asn Thr Ile Ser Lys Gln Gly Phe Glu Ser Ile Phe Glu Arg Met Lys
385                 390                 395                 400

Glu Leu Glu Asn Gln Met Leu Ala Phe Asn Pro Tyr Gly Gly Arg Met
                405                 410                 415

Ser Glu Ile Ser Glu Phe Ala Lys Pro Phe Pro His Arg Ser Gly Asn
                420                 425                 430

Ile Ala Lys Ile Gln Tyr Glu Val Asn Trp Asp Glu Leu Gly Val Glu
            435                 440                 445

Ala Ala Asn Arg Tyr Leu Asn Phe Thr Arg Val Met Tyr Asp Tyr Met
    450                 455                 460

Thr Pro Phe Val Ser Lys Asn Pro Arg Glu Ala Phe Leu Asn Tyr Arg
465                 470                 475                 480

Asp Leu Asp Ile Gly Val Asn Ser His Gly Lys Asn Ala Tyr Gly Glu
                485                 490                 495

Gly Met Val Tyr Gly His Lys Tyr Phe Lys Glu Thr Asn Tyr Lys Arg
                500                 505                 510

Leu Thr Met Val Lys Thr Arg Val Asp Pro Ser Asn Phe Phe Arg Asn
        515                 520                 525

Glu Gln Ser Ile Pro Thr Leu Ser Ser Ser Trp Lys
    530                 535                 540
```